(12) United States Patent
Woidschützke

(10) Patent No.: US 8,696,361 B2
(45) Date of Patent: Apr. 15, 2014

(54) PRACTICE MODEL

(75) Inventor: Horst Woidschützke, Wangen (DE)

(73) Assignee: Franz Sachs GmbH & Co. KG (DE)

( * ) Notice: Subject to any disclaimer, the term of this patent is extended or adjusted under 35 U.S.C. 154(b) by 0 days.

(21) Appl. No.: 13/373,331

(22) Filed: Nov. 10, 2011

(65) Prior Publication Data

US 2012/0148993 A1 Jun. 14, 2012

(30) Foreign Application Priority Data

Nov. 18, 2010 (EP) .................................... 10191681

(51) Int. Cl.
*G09B 23/28* (2006.01)
(52) U.S. Cl.
USPC .......................................... 434/263; 434/262
(58) Field of Classification Search
USPC ..................... 434/262–275; 433/199.1, 229
See application file for complete search history.

(56) References Cited

U.S. PATENT DOCUMENTS 7,713,064 B2 * 5/2010 Schulz ......................... 434/263

FOREIGN PATENT DOCUMENTS

EP 1970878 9/2008

OTHER PUBLICATIONS

Anonymous, "Range of Products 2010 | 2011", http://www.kleedoc.com/de/files/frasaco.pdf.
Dr. Shabeel, "frasaco typodont jaws and teeth: accessories for ANA-4", http://frasacotypodont.blogspot.com/2010/10/accessories-for-ana-4html.

* cited by examiner

*Primary Examiner* — Timothy A Musselman
(74) *Attorney, Agent, or Firm* — Pandiscio & Pandisico

(57) ABSTRACT

A model for learning dentistry skills and including a shell attachable to a phantom head, through-holes disposed in the shell, teaching teeth individually arranged in the through-holes, and having a carrier plate attachable to the shell, such that a teaching tooth is releasably fixed on the shell and is adapted to be inserted into the model and removed therefrom. At least one peg disposed on the carrier plate, and a holding chamber disposed in the peg, wherein a holding element projects from each tooth and passes through a through-hole in the shell and is aligned with a holding chamber and is inserted into the holding chamber, and a holding strip disposed between the shell and the carrier plate and adapted to contours of the carrier plate and the shell and disposed in openings, the holding strip being movable for securing the holding element of the teaching tooth to the carrier plate.

16 Claims, 4 Drawing Sheets

PRACTICE MODEL

1. FIELD OF THE INVENTION

The present invention relates to a practice model for learning dentistry skills.

2. DESCRIPTION OF THE PRIOR ART

A practice model of this kind is disclosed in EP 1 970 878 A1 and has proven effective in practice. The individual teaching teeth are provided with threaded holes on their undersides facing towards a shell, into which a screw can be screwed which passes through a carrier plate and the shell with the effect that the teaching teeth are firmly mounted on the carrier plate and thereby also on the shell. When the teaching teeth are exchanged, the corresponding screw must be unfastened so that the teaching teeth can subsequently be removed from the though-hole in the shell and from the carrier plate.

It has proven to be a disadvantage with this state of the art, in that it is exceedingly troublesome and time-consuming to secure the individual teaching teeth into the carrier plate with a screw. Furthermore, the shell and also the carrier plate are often attached to a phantom head or an articulator, with the effect that the underside of the shell and the carrier plate are either inaccessible or can only be accessed with difficulty in order for the screws to be reached and unscrewed.

DE 103 93 483 T5 discloses a model tooth for practicing dentistry and a fixture with a model tooth attached for practicing dentistry. The model tooth is inserted into a through-hole that is disposed in the carrier plate. A head with a truncated cone shape is formed onto a tooth stump facing towards the carrier plate, and the external diameter of the head is larger than the through-hole in the carrier plate. When the tooth stump is pushed into the carrier plate, therefore, the through-hole is stretched, with the effect that the tooth stump can be inserted into the carrier plate by exerting force. The through-hole has a step which faces towards the head of the tooth stump and the tooth stump makes contact with this step when it has been installed. If the tooth is to be removed from the carrier plate, it must be pulled out of the through-hole with manual force against the preload force of the carrier plate. The through-hole therefore expands and consequently undergoes elastic deformation.

Such attachment means according to the state of the art have not proven effective in practice, because the securing of the teaching tooth in the corresponding through-hole is highly prone to defects since even a slight amount of play on the tooth stump in the carrier plate or in the through-hole results in the teaching tooth wobbling. This results in serious errors during dentistry exercises and does not correspond to the reality of a human or animal tooth in a jaw.

What is more, the through-hole wears out after teeth have been inserted and removed many times, because the elastic deformation causes the through-hole to expand with the result that the play on the teaching tooth in the through-hole is greater after the teaching tooth has been inserted in and removed from the through-hole many times. Furthermore, this securing possibility does not provide the rigidity required for holding the teaching tooth, because even slight forces cause the through-hole to deform, and the teaching tooth slips. This leads to an exercise simulation which does not correspond to real conditions, or only inadequately so.

SUMMARY OF THE INVENTION

It is, therefore, the task of the present invention to develop a practice model of the aforementioned kind such that each training tooth is reliably and durably held in the practice model, the plurality of teaching teeth can be inserted into or removed from the practice model at the same time without the need to undo or tighten an individual attachment for every single teaching tooth, and such that at the same time the teaching tooth is held on the carrier plate of the practice model without play when installed, in order to allow the dentistry exercises to be performed under conditions which are as identical as possible to those in an actual human or animal jaw.

In accordance with the present invention, a holding strip is held in an axially adjustable arrangement relative to the carrier plate, and the teaching teeth are inserted with their holding elements into holding champers of pegs. Therefore it is assured that if the holding strip is moved, all pegs will be pressed together inwards, with the effect that the diameter of the holding chamber, and in particular the diameter of the holding pocket in which the head of the holding element is positioned in the mounted position, will be pushed together. As a result, there is a releasable compression fit, and the teaching teeth are reliably locked in the corresponding peg.

Due to the compression force acting in the circumferential direction, the teaching teeth are firmly positioned in the peg of the carrier plate, with the effect that they do not wobble during dentistry exercises and do not slide out of position, which means that appropriate forces can be exerted for the treatment of teeth.

As soon as the teaching teeth have fulfilled their purpose in the exercise, they can be removed jointly or individually from the holding chamber of the corresponding peg by moving the holding strip, with the effect that the teaching teeth in the practice model can be exchanged quickly and easily.

Furthermore, the holding chamber, and especially the insertion channel, is not subject to any wear due to elastic deformations when the teaching tooth is pulled out or pushed in, because there is a slot disposed in the peg, the depth of which is adapted to the length of the insertion channel with the effect that the wall of the peg undergoes elastic deformation in the area of the slot, and after the larger sized head of the teaching tooth has left the insertion channel, the wall springs back to its initial position. The openings disposed in the holding strip additionally secure the pegs and press them together so that even if there is a certain amount of wear on the peg, it is still assured that the teaching teeth will be reliably held in the holding chamber of the peg, because the pegs are completely or almost completely enclosed by the openings, with the effect that they are not elastically deformable towards the outside.

BRIEF DESCRIPTION OF THE DRAWINGS

The drawings show a sample embodiment configured in accordance with the present invention, the details of which are explained below. In the drawings.

DESCRIPTION OF THE PREFERRED EMBODIMENT

Figure 1:
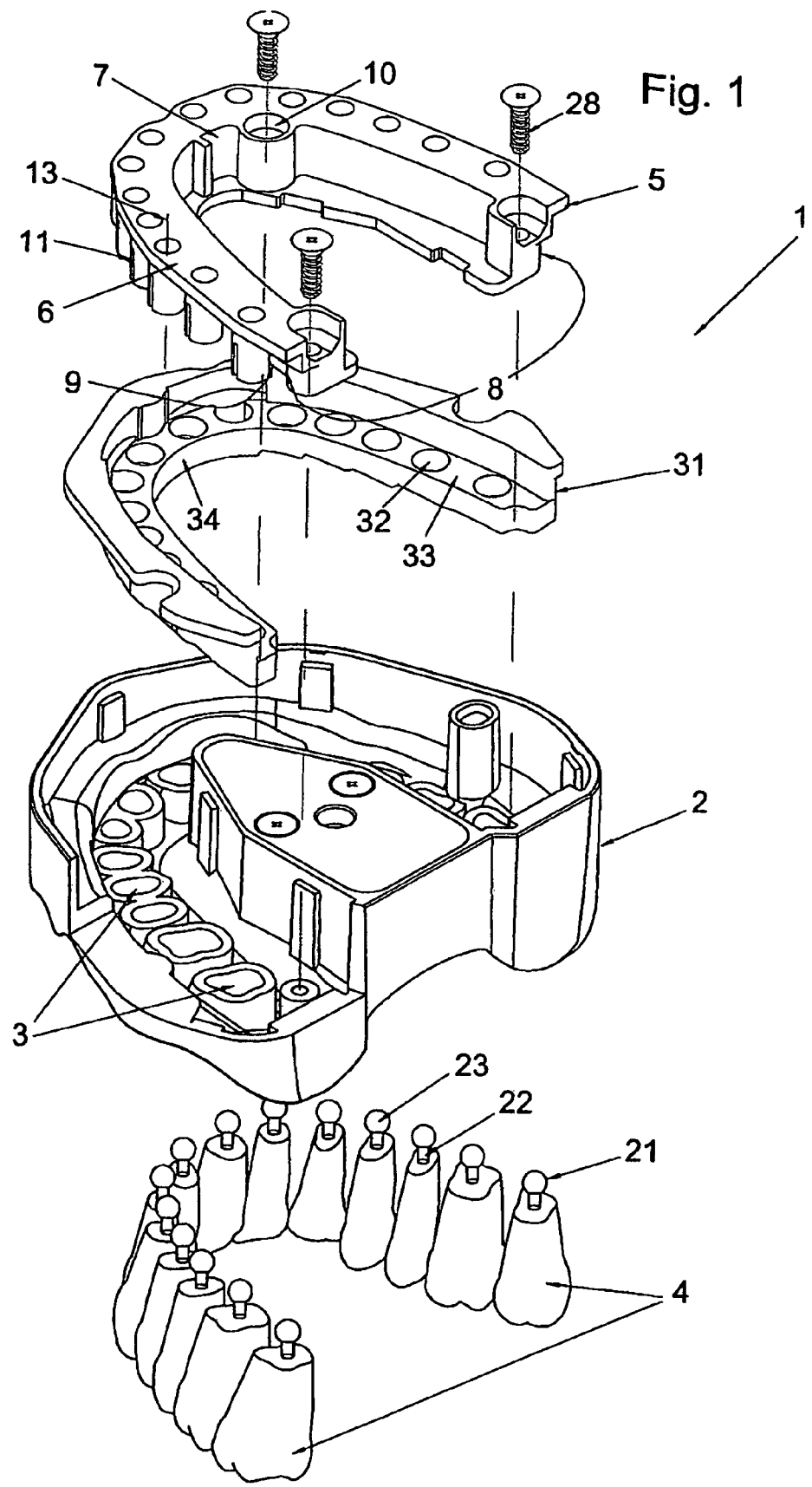
FIG. 1 shows a practice model comprising a shell and a carrier plate attached to the shell, between which a holding strip is arranged in an axially adjustable arrangement, and further comprising a plurality of teaching teeth adapted to be secured in the shell by the holding strip and the carrier plate, in an exploded view.
Figure 2:
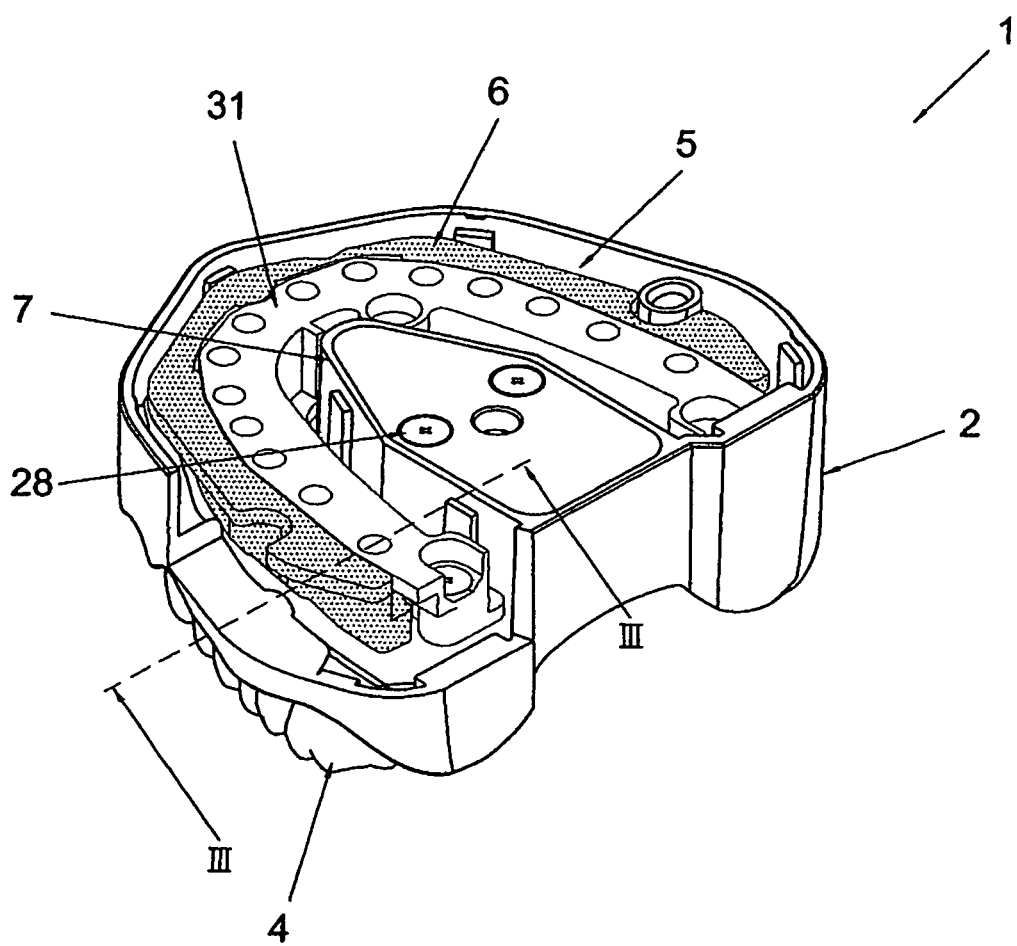
FIG. 2 shows the practice model in accordance with FIG. 1 in an assembled condition, in a perspective view.

FIGS. 1 and 2 show a practice model 1 which can be used by dental students in order to learn dentistry skills. However, the practice model can also be copied on an animal jaw in order to allow veterinarians to undertake similar veterinary exercises.

The practice model 1 comprises a shell 2 with a plurality of through-holes 3 worked into it. The inner contours of the through-holes 3 are adapted to the outer contours of teaching teeth 4, because the teaching teeth 4 are each inserted into the corresponding through-hole 3 when mounted, and should be supported in the sideways direction by the side wall of the through-hole 3.

In order to secure the teaching teeth 4 in the through-hole 3, a carrier plate 5 is provided which is arranged on the opposite side of the shell 2 in relation to the position of the teaching teeth 4.

The carrier plate 5 consists of a base 6 and a horseshoe or U-shaped arch 7 which is firmly connected to the base 6. The shell 2 is produced in such a way that the carrier plate 5 can be inserted into it; the contours of the shell 2 and the carrier plate 5 thus correspond to one another.

Figure 3:
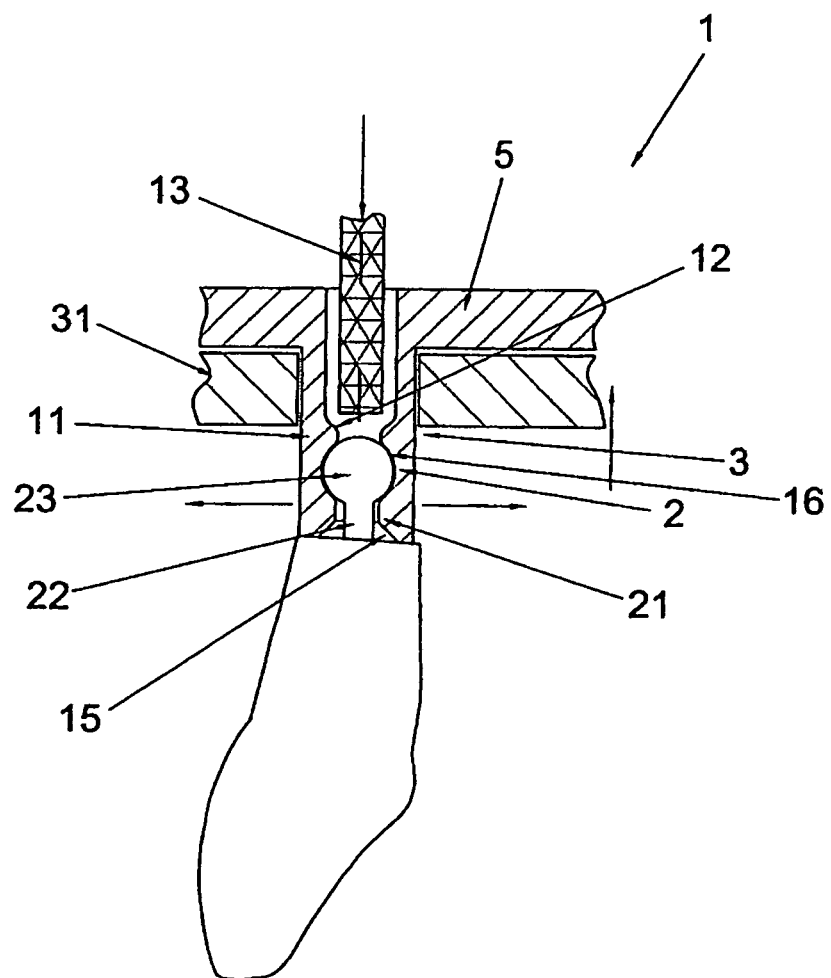
FIG. 3*a* shows the practice model in accordance with FIG. 2 along a section line in an initial condition for inserting or removing the teaching tooth.
FIG. 3*b* shows the practice model in accordance with FIG. 3*a* in a plan view and showing an excerpt.
Figure 3:
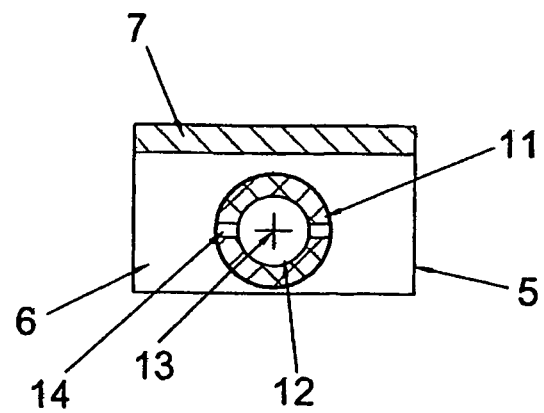

A plurality of pegs 11 are formed onto the base of the carrier plate 5 and the pegs 11 project at right angles from the carrier plate 5 in the direction of the shell 2. A holding chamber 12 (FIGS. 3a-4) is worked into each of the pegs 11, and a lengthways axis 13 of the holding chamber 12 is aligned at right angles with the base 6. The holding chamber 12 has an insertion channel 15 (FIG. 3a) and a ball-shaped holding pocket 16. The inner diameter of the insertion channel 15 is much smaller in size than the diameter of the holding pocket 16.

Furthermore, two opposite slots 14 (FIG. 3b) are worked into the walls of the corresponding pegs 11 and run parallel to the lengthways axis 13. The depth of the slots 14 corresponds to the length of the insertion channel 15, or is slightly shorter.

The teaching teeth 4 are normally made of plastic. In order for the teaching teeth 4 to be inserted into the holding chamber 12 of the corresponding peg 11, and to be fixed there, there are holding elements 21 provided on the teaching teeth 4, the holding elements each comprising a web 22 and a ball or pear-shaped head 23. Both the web 22 and the head 23 are manufactured from a metallic material and form a structural unit.

The outer contour of the web 22 is much smaller in size than the outer contour of the head 23. The web 22 has a thread, which is not illustrated, on its end opposite to the head 23 and this thread is screwed into a threaded hole worked into the teaching tooth 4, with the effect that the web 22 is firmly connected to the teaching tooth 4.

When a teaching tooth 4 is positioned in the shell 2, the web 22 and the head 23 pass through the through-hole 3 in the shell 2 and project from it in the direction of the carrier plate 5. The pegs 11 are positioned so that each of the holding chambers 12 worked into them is flush with one of the heads 23 of the teaching tooth 4. As a result, each head 23 can be pushed into one of the holding chambers 12.

The outer diameter of the head 23 is much larger than the width of the insertion channel 15, consequently the insertion channel 15 expands. One or more of the slots 14 are worked into the insertion channel 15, which means that an elastic deformation occurs which has the properties of a spring. As soon as the head 23 has been pushed into the holding pocket 16, the wall of the peg 11 springs back into its initial position in the area of the insertion channel 15.

This design embodiment and the positioning of the head 23 in the holding pocket 16 does not yet mean that the teaching tooth 4 has been reliably secured on the carrier plate 4—because the teaching teeth 4 can be pulled out of the holding chamber 12 by manual force without further ado—therefore a holding strip is provided by means of which widening of the corresponding peg 11 in the area of the insertion channel 15 and the holding pocket 16 is prevented.

Figure 4:
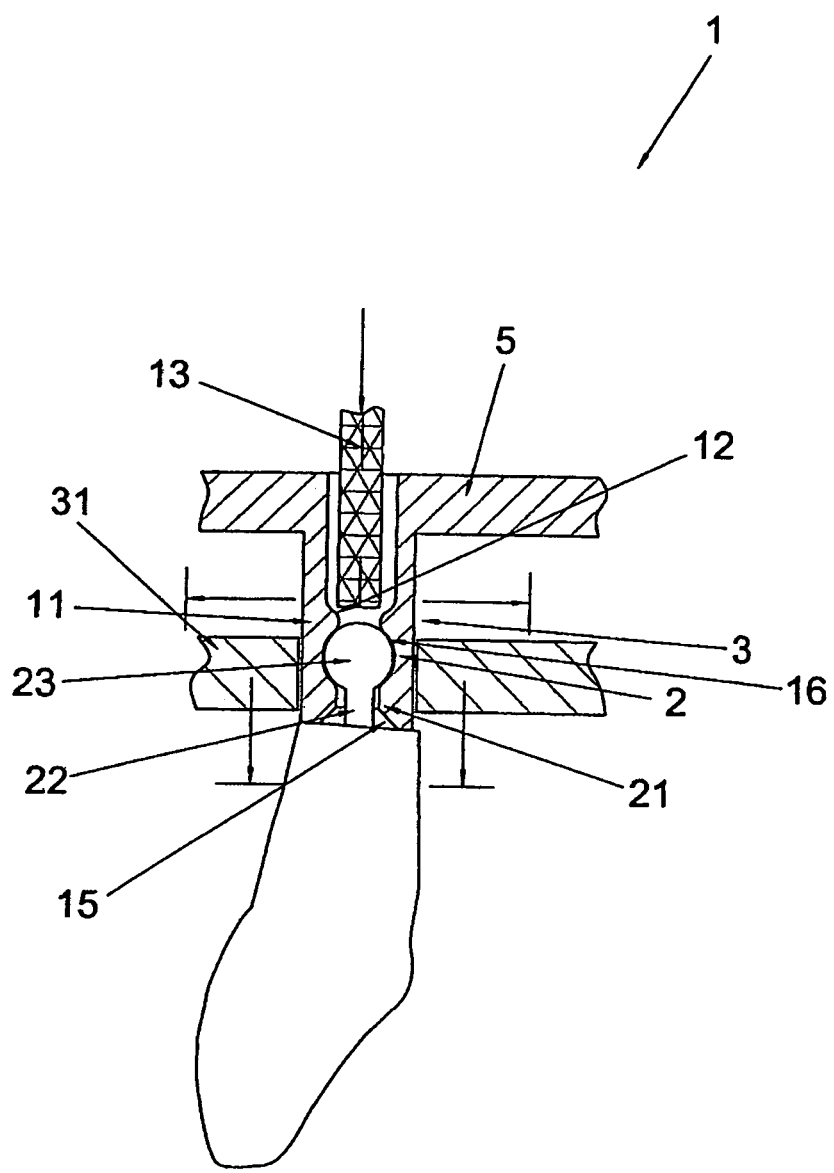
FIG. 4 shows the practice model in accordance with FIG. 3a in which the holding strip has been pushed in the direction of the teaching tooth for locking the teaching tooth.

FIGS. 3a and 4 in particular show the mode of function of a holding strip 31. The holding strip 31 is initially adapted to the contour of the carrier plate 5 and the shell 2. Furthermore, the holding strip 31 consists of two legs 33 and 34 (FIG. 1) running at right angles to one another. A plurality of openings 32 are worked into the first leg 33; the first leg 33 runs parallel to the base 6 of the carrier plate 5 when installed. The second leg 34 is aligned parallel to the corresponding peg 11.

The inner diameter of the openings 32 largely corresponds to the outer diameter of the pegs 11, with the effect that the holding strip 31 can be pushed onto the pegs 11 of the carrier plate 5 and each peg 11 is completely enclosed. Often, there is not enough material in the front area of the lower jaw in order to allow complete enclosure of the head 23 by the pegs 11, with the effect that the head 23 is only partially enclosed in these holding chambers 12. However, even with an enclosure angle of 180° or more, reliable securing of the teaching tooth 4 in the peg 11 is assured.

If the holding strip 31 is moved in the direction of the carrier plate 5, the base 6 serves as a stop surface for the holding strip 31, with the effect that the holding strip 31 is secured in the initial position. In this condition, the pegs 11 project from the holding strip 31, because the holding strip 31 is arranged underneath the holding chamber 12, in particular underneath the holding pocket 16. As a result, when the teaching tooth 4 is inserted, the side walls of the pegs 11 can be elastically deformed outwards in order to allow the head 23 of the teaching tooth 4 to be inserted into the holding pocket 16.

Once all teaching teeth 4 have been inserted into the corresponding pegs 11, the holding strip 31 is moved axially in the direction of the teaching tooth 4 in accordance with FIG. 4, with the effect that the holding strip 31 is now at a distance from the carrier plate 5 and runs approximately on the same plane as the holding pocket 16. The pegs 11 are completely enclosed by the opening 32 of the holding strip 31, consequently the pegs 11 can no longer undergo elastic deformation, which ensures that they are reliably held in the holding pocket 16 even when a powerful force acts on the teaching teeth 4.

A cavity 9 (FIG. 1) is provided between the outside of the pegs 11 and an outer wall of the arch 7 identified with the reference number 8, and the holding strip 31 protrudes into the cavity 9 in areas. The cavity 9 is required in order to allow the holding strip 31 to move freely. The holding strip 31 can be moved relative to the carrier plate 5 over an adjustment travel of one to three millimetres.

The invention claimed is:

1. A practice model for learning dentistry skills, the model comprising:
   a shell adapted to be attached to a phantom head or articulator, and a plurality of through-holes disposed in said shell,
   one or more teaching teeth individually arranged in said through-holes of said shell and a carrier plate adapted to be locked on said shell and by means of which one or more of said teaching teeth can be releasably fixed on said shell
wherein at least one peg is disposed on said carrier plate, and a holding chamber is disposed in said peg;
a holding element projects from each of said teaching teeth and passes through said through-hole in said shell when said teaching tooth is installed;
said holding element is aligned with said holding chamber of said peg and is inserted in said one holding chamber;
a holding strip is disposed between said shell and said carrier plate, the contour of said holding strip being adapted to contours of said carrier plate and said shell and is disposed in openings which are round and flush with said holding chamber,
said holding strip being mounted in an axially movable arrangement for securing said holding element of said teaching teeth relative to said carrier plate between said carrier plate and said shell.

2. The practice model in accordance with claim 1, wherein at least one slot is disposed in said peg and is aligned at right angles or parallel to a lengthways axis of said holding chamber.

3. The practice model in accordance with claim 1, wherein said holding strip is provided with an L-shaped cross section, the openings are disposed in a leg which runs parallel to and at a distance from said shell and a leg of said holding strip extends at right angles to the leg and is aligned in parallel with said pegs of said carrier plate.

4. The practice model in accordance with claim 3, wherein said holding elements of said teaching teeth comprise a web and a pear or ball-shaped head, the diameter of said head being larger than the width of said web, said holding chamber comprises an insertion channel and a holding pocket, the geometrical dimensions of which are adapted to diameters of said webs and said heads of said holding elements.

5. The practice model in accordance with claim 4, wherein said head is larger than an internal diameter of said corresponding insertion channel and the diameter of said holding pocket is substantially the same size as said head.

6. The practice model in accordance with claim 5, wherein said insertion channel of said holding chamber is elastically deformed outwards by the corresponding holding element when said head is inwardly pushed in the area of a slot.

7. The practice model in accordance with claim 6, wherein when said holding strip is pushed axially in the direction of said shell, said holding chambers of said peg are jointly released in areas in a circumferential direction, or when said holding strip is pushed axially opposite to said shell, said holding chamber is elastically deformed such that the internal diameter thereof is reduced and a releasable compression fit is formed between said holding pocket of said holding chamber and said head of the corresponding teaching tooth.

8. The practice model in accordance with claim 1, wherein said peg is formed on a base portion of said carrier plate and the base comprises a stop surface for said holding strip.

9. The practice model in accordance with claim 1, wherein height dimensions of said carrier plate and said peg are of equal size and the height dimension of said holding strip is less than the height dimensions of said carrier plate and said peg.

10. The practice model in accordance with claim 9, wherein adjustment travel of said holding strip relative to said carrier plate is about one to three millimeters.

11. The practice model in accordance with claim 1, wherein said carrier plate comprises a U-shaped or horseshoe-shaped arch, and a base projecting at right angles from said arch, and said peg is arranged at right angles on said base and parallel to an outer wall of said arch.

12. The practice model in accordance with claim 11, wherein a cavity is provided between said peg and the outer wall of said arch, and said holding strip projects into said cavity in at least some areas.

13. The practice model in accordance with claim 11, wherein one or more through-holes is/are disposed in said arch of said carrier plate and each through hole is provided with a screw passing therethrough which can be screwed into a threaded hole provided in said shell.

14. The practice model in accordance with claim 1, wherein shapes of said teaching teeth correspond to shapes of human or animal teeth, and contours of said through-holes in said shell correspond to the contour of said teaching tooth.

15. The practice model in accordance with claim 14, wherein some of said teaching teeth are arranged in said through-holes in said shell and are supported in a sideways direction by an inner wall of said through-hole.

16. A practice model for learning dentistry skills, the model comprising
a shell adapted to be attached to a phantom head or articulator, and a plurality of through-holes disposed in said shell,
one or more teaching teeth individually arranged in a through-hole of said shell,
and a carrier plate adapted to be locked on said shell and by means of which a teaching tooth can be releasably fixed on said shell,
wherein at least one peg is disposed on said carrier plate and a holding chamber is disposed in said peg,
and a holding element projects from each of said teaching teeth and is adapted to penetrate said through-hole of said shell,
wherein said individual holding element is aligned flush with said holding chamber of said peg and is inserted in said holding chamber
wherein a holding strip is disposed between said shell and said carrier plate, the contour of said holding strip being adapted to contours of said carrier plate and said shell, and in said shell openings are disposed which are round and run flush with said holding chamber,
and said holding strip being mounted in an axially movable arrangement for securing the corresponding holding element of said teaching teeth relative to said carrier plate between said carrier plate and said shell,
such that, when said holding strip is displaced in the direction of said holding element said pegs being locked in position and squeezed by an opening disposed in said holding strip, which results in a releasable pressure fit locking said teaching teeth in the corresponding peg.

* * * * *